United States Patent [19]

Hashiguchi et al.

[11] Patent Number: 5,352,431
[45] Date of Patent: Oct. 4, 1994

[54] LOW MOLECULAR WEIGHT POLYSACCHARIDE COMPLEXES FOR X-RAY IMAGING

[75] Inventors: Yuji Hashiguchi, Sodegaura; Kumiko Iwai, Ichihara; Shigemi Seri, Ichihara; Susumu Kondo, Ichihara; Makoto Azuma, Ichihara, all of Japan

[73] Assignee: Nihon Medi-Physics Co., Ltd., Hyogo, Japan

[21] Appl. No.: 119,387

[22] Filed: Sep. 13, 1993

Related U.S. Application Data

[62] Division of Ser. No. 952,992, Sep. 29, 1992, Pat. No. 5,271,924.

[30] Foreign Application Priority Data

Oct. 4, 1991 [JP] Japan .................... 3-258017

[51] Int. Cl.$^5$ .................... A61K 49/04; A61K 31/715; C08B 37/08
[52] U.S. Cl. .................... 424/4; 534/16; 536/20; 536/55.2; 514/54; 514/55; 514/62; 514/836
[58] Field of Search .................... 424/4; 436/173; 128/653.4, 654; 534/16; 536/20, 55.2; 514/54, 55, 62, 836

[56] References Cited

U.S. PATENT DOCUMENTS

| | | | |
|---|---|---|---|
| 5,141,739 | 8/1992 | Jung et al. | 424/4 |
| 5,143,716 | 9/1992 | Unger | 424/9 |

FOREIGN PATENT DOCUMENTS

| | | |
|---|---|---|
| 0186947 | 7/1986 | European Pat. Off. . |
| WO8605789 | 10/1986 | PCT Int'l Appl. . |
| WO9110454 | 7/1991 | PCT Int'l Appl. . |

OTHER PUBLICATIONS

Gibby, W. A., et al., Investigative Radiology, 24: 302-309 (1989).

Primary Examiner—Gary E. Hollinden

[57] ABSTRACT

There is disclosed an imaging agent for diagnosis comprising a compound composed of a polynuclear type compound of the formula I or II:

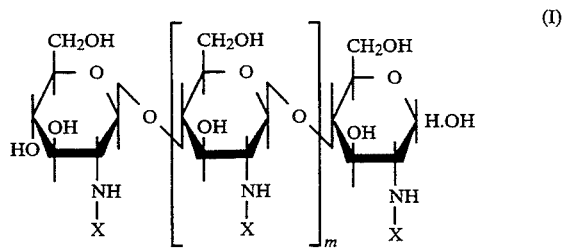

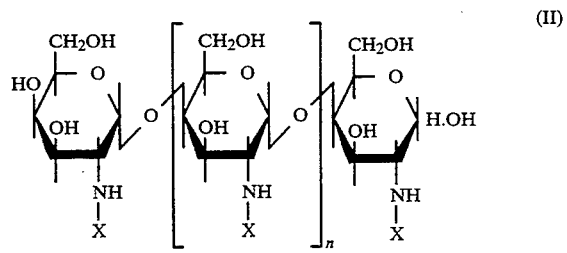

wherein each X is a hydrogen atom or a bifunctional ligand, at least one of them are bifunctional ligand and m or n is an integer or 1 to 6, and at least one metal ion being coordinated with at least one bifunctional ligand moiety, said metal ion being selected from the group consisting of metal ions having the atomic number of 21-29, 31, 32, 37-39, 42-44, 49 and 56-83.

9 Claims, 1 Drawing Sheet

LOW MOLECULAR WEIGHT POLYSACCHARIDE COMPLEXES FOR X-RAY IMAGING

This is a division of copending application Ser. No. 07/952,992 filed on Sep. 29, 1992, now U.S. Pat. No. 5,271,924.

FIELD OF THE INVENTION

The present invention relates to an imaging agent for diagnosis, in particular, to an imaging agent for diagnosis containing a polynuclear type metal complex compound.

BACKGROUND OF THE INVENTION (Diethylenetriaminepentaacetic acid)gadolinate (hereinafter abbreviated as to "DTPA-Gd") is the only one practical pharmaceutical which is presently known as a nuclear magnetic resonance imaging (hereinafter sometimes abbreviated as MRI) agent for diagnosis [JP-A 58-29718] and it is considered that the use thereof as an imaging agent for diagnosis in the brain or spinal regions has been almost established. Since, however, DTPA-Gd is complexed, the relaxivity showing the image display index is lower (about ½) than that of Gd itself. Therefore, it is necessary to compensate this lowered relaxivity by increasing the dose. In addition, DTPA-Gd is rapidly excreted into the urine after administration [Hiroki Yoshikawa et al., Gazoshindan, 6, pages 959–969 (1986)], and this is very disadvantageous for imaging of several parts of the body by reflecting them in blood stream (blood vessel distribution, blood stream distribution, distribution volume, permeation and the like in a lesion) with a single injection of the pharmaceutical. Further, such rapid excertion also makes distribution properties of DTPA-Gd disadvantageous.

For solving the above-described problems (improvement in the relaxivity), some attempts at polynuclearization by repetition of mononuclear complex are described in JP-A 63-41468, JP-A 2-196776 and the like. Since, however, the poly-nuclearization is limited at best to di-nuclearization or tri-nuclearization, remarkable improvement in relaxivity can not be recognized.

Thereafter, the use of a polynuclear type metal complex compound obtained by introducing a plurality of metal complexes into a carrier polymer material as an imaging agent for diagnosis used as has been investigated. As a result, a MRI agent for diagnosis the carrier of which is human serum albumin (abbreviated as "HSA") [Ogan, M. D., et al., Invest. Radiol., 22, pages 665–671 (1987)], dextran [Brash, R. C., et al., Radiology, 175, pages 483–488 (1990)], starch [JP-A 61-501571], polylysine [JP-A 64-54028] or the like has been proposed and succeeded in improvement of relaxivity. These polymer polynuclear type metal complex compounds are localized in blood vessel for a constant period of time from immediately after administration and have the common distribution properties as retention in blood vessel for a relatively long period of time, which also improves the rapid excretion and penetration properties of DTPA-Gd.

However, the polymer carriers which can be a backbone for these polynuclear type metal complexes, regardless of a natural or synthetic material, is a heterogeneous compound the molecular weight of which has no mono-dispersion and is dealt with as an average value having a certain distribution width. Therefor, there is a problem that pharmaceutical uniformization can not be attained. For this reason, it is very difficult to control the number of metal ion to be introduced at constant and, therefore, heterogeneity arises inevitably in the objective physicochemical properties. Further, since all of the above-described polymers have the molecular weight more than tens of thousands, they have an unnecessarily long retention time in blood such as from ten and a few hours to a few days and have problems on biological acceptability as retention in the body, antigenicity and the like.

OBJECTS OF THE INVENTION

The main object of the present invention is to provide an imaging agent for diagnosis comprising a polynuclear type metal complex compound which can solve the above-described problems in the known imaging agents for diagnosis containing a polymer polynuclear type metal complex compound. Namely, the main object of the present invention is to provide an image agent for diagnosis having a plurality of metal ions which are stably introduced in the desired number, good homogeneity, good solubility, physiologically acceptability and suitable retention time in blood for image diagnosis.

This object as well as other objects and advantages of the present invention will become apparent to those skilled in the art from the following description with reference to the accompanying drawings.

SUMMARY OF THE INVENTION

Figure 1:
FIG. 1 is a MRI showing a transverse view of the chest region including the heart of a rat sacrificed at 1 hour after administration of a (galactosamino-pentamer)-[1-(p-isothiocyanatebenzyl)-diethylenetriaminepentaacetic acid]gadolinate (abbreviated as "GPEN-DTES-Gd") solution.
Figure 2:
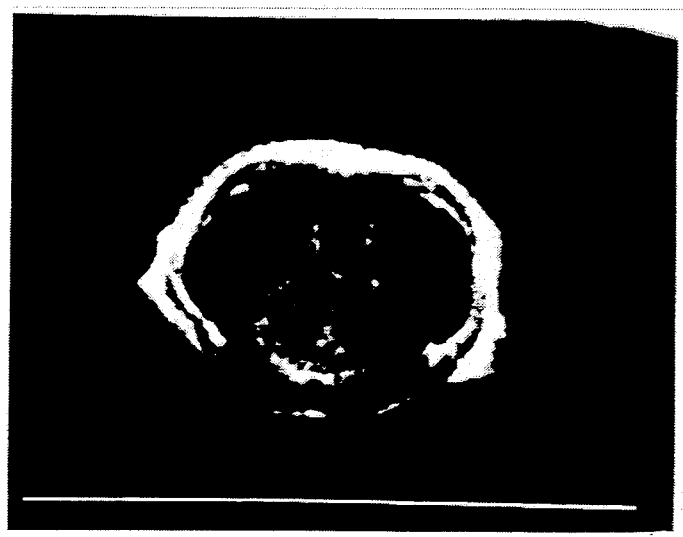
FIG. 2 is a MRI showing a transverse view of the chest region including the heart of a rat sacrificed at 1 hour after administration of DTPA-Gd (MAGNEVIST ®).

In order to accomplish the above-described objects, the present inventors studied extensively. As a result, it has been found that a polynuclear type metal complex compound having as a backbone a chitosan-oligosaccnaride or qaiactosamino-oligosaccharide and has a clinically effective retention in blood.

For example, the present inventors have investigated in vitro or in vivo relaxivity and contrast effect of a polynuclear type metal complex compound GPEN-DTES-Gd, wherein 1-(p-isothiocyanatebenzyl)-DTPA (abbreviated as to "DTES") [Martin, W. B., et al., Inorg. Chem., 25, pages 2772–2781 (1986)] is chemically bonded as a bifunctional ligand to galactosamino-pentamer (abbreviated as "GPEN") and Gd is coordinated therewith as a metal ion. As a result, it has been confirmed that $T_1$ relaxivity in water (magnetic field intensity: 6.35T, 25° C.) is remarkably increased to 7.6 $(mM \cdot S)^{-1}$, being about two times that of DTPA-Gd. Further, it has been confirmed that the contrast effects (magnetic field intensity: 1.5T, $T_1$ weighted imaging by spin echo method) in the heart of a rat at 1 hour after administration is enhanced by about 1.8 times that of DTPA-Gd imaged under the same conditions. Furthermore, GPEN-DTES-In-111 labeled with a radioactive metal ion, In-111, has half-life period in blood of about 55 minutes in the distribution test in rats. This half-life period in blood is sufficiently longer than that of DTPA-In-111, and shows good retention in blood.

The present invention has been completed based on these findings and provides an imaging agent for diagnosis comprising a compound composed of a polynuclear type compound of the formula I or II:

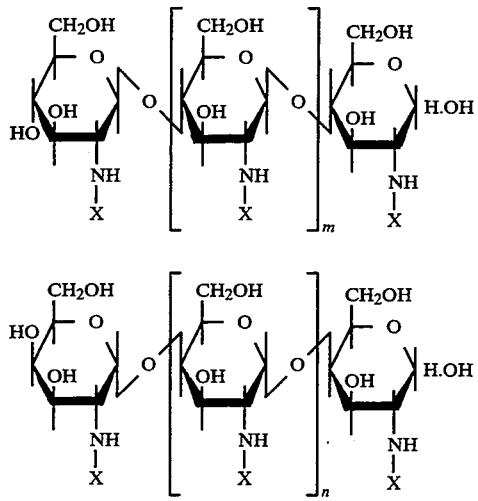

wherein each X is a hydrogen atom or a bifunctional ligand, at least one of them are a bifunctional ligand and each of m and n is an integer of 1 to 6, and at least one metal ion being coordinated with at least of one bifunctional ligand moiety, said metal ion being selected from the group consisting of metal ions having the atomic number of 21–29, 31, 32, 37–39, 42–44, 49 and 56–83.

DETAILED DESCRIPTION OF THE INVENTION

The term "polynuclear type" as used herein means a structure wherein a plurality of metal ions are introduced therein via a complexing agent per unit molecule.

The compound used as a backbone for polynuclearization in the present invention is an amino oligosaccharide, more particularly, a chitosanoligosaccharide or galactosamino-oligosaccharide. In particular, an oligomer having the repetition number of component monosaccharide of 3 to 6 (m or n is 1 to 4 in the formula I or II) is advantageously used. The chitosan-oligosaccharide is an oligosaccharide wherein D-glucosamine monomers are bonded through $\beta$-1,4 bond. The chitosanoligosaccharide to be used can be obtained, for example, by hydrochloric acid-hydrolyzing or enzymatically degrading chitosan prepared from natural crab shell. On the other hand, the galactosamino-oligosaccharide has a structure wherein D-galactosamine monomers are polymerized through $\alpha$-1,4 bond. The galactosamino-oligosaccharide to be used can be obtained, for example, by hydrolyzing natural polygalactosamine produced by imperfect fungi, Paecilomyces with an acid or enzyme. Since both chitosan and galactosamino-oligosaccharide are a reactive molecule having a high reactive amino group at 2-position in the component monosaccharide, the complicated derivation is not required for bonding with a ligand. As a result, a reaction with a bifunctional ligand can be completed in a single step.

Respective oligosaccharides are fractionated in high purity by chromatography according to the degree of polymerization and these oligosaccharides having uniform molecular weight are commercially available. Therefore, the number of bifunctional ligands and metal ions to be introduced can be precisely controlled and it is possible to prepare a pharmaceutically homogenous polynuclear type metal complex compound. In addition, both of them have high compatibility with the living body and physiological acceptability.

As the bifunctional ligand, there can be used linear or cyclic polyaminopolycarboxylic acids having a cross-linking chain moiety which can bond to the amino group at 2-position of the amino oligosaccharide as a backbone. The preferred bifunctional ligand is a ligand having as a coordinating partial structure the skeleton of DTPA or derivative thereof, or the skeleton of 1,4,7,10-tetraazacyclododecane-1,4,7,10-tetraacetic acid (abbreviated as "DOTA") or a derivative thereof. As the reactive group in the cross-linking chain part of bifunctional ligand which can bond to the amino group at 2-positional, i.e., the reactive functional group, active halogen, alkoxyester, succinimidiester, isothiocyanate, acid anhydride and the like are preferred. More particularly, there are 1-(p-isothiocyanatebenzyl)-DTPA [Martin, W. B., et al., Inorg. Chem., 25, pages 2772–2781 (1986), DTPA anhydride, 2-(p-isothiocyanatebenzyl)-1,4,7,10-tetraazacyclododecane-1,4,7,10-tetraacetic acid [U.S. Pat. No. 4,678,667] and the like.

The bond between the amino-oligosaccharide and the bifunctional ligand can be formed according to a per se known method. For example, a reaction of the bifunctional ligand having as the cross-linking chain terminal an acid anhydride [Hnatowich, D. J., et al., Int. J. Appl. Rad. Isot., 33, pages 327–332 (1982)], isothiocyanate [Esteban, J. M., et al., J. Nucl. Med., 28, pages 861–870 (1987)], alkoxyester [Washburn, L. C., et al., Nucl. Med. Biol., 18, pages 313–321 (1991)] or active halogen [Fourie, P. J., et al., Eur. J. Nucl. Med., 4, pages 445–448 (1979)] with the amino-oligosaccharide can be carried out according to the description in the above cited known publications.

In the present invention, the metal ion is selected from the group consisting of metal ions having the atomic number of 21–29, 31, 32, 37–39, 42–44, 49 and 56–83 depending upon a particular use of image diagnosis. When the polynuclear type metal complex of the present invention is used for MRI diagnosis, the metal ion must be paramagnetic and is selected from the ions of the atomic number of 26 and lanthanide having the atomic number of 57–70. The metal ion is preferably an ion of Gd, Dy, Tb, Ho, Er or Fe. When used for X-ray diagnosis, the metal ion is selected from the lanthanide element ions having the atomic number of 57–70 and the ions of the element having the atomic number of 56, 76, 82 and 83. The metal ion preferably an ion of Bi, Pb or Os. For radiation diagnosis, the metal ion must be radioactive and is suitably the radioactive metal ion such as Co, Cu, Ga,. Ge, Sr, Y, Tc, In, Sm, Gd, Yb, Re or Ir. As the metal ion, there can be used a metal itself or inorganic compound thereof (for example, chloride, oxide). Complexation can be carried out by a conventional method.

In the polynuclear type metal complex compound thus obtained, at least one, preferably, two or more bifunctional ligands are chemically bonded to chitosan-oligosaccharide or galactosamino-oligosaccharide and the metal ions are bonded to this coordinating moiety through a complexing bond.

The polynuclear type metal complex compound can be formulated into an imaging agent for diagnosis in any suitable dosage form by mixing with any suitable pharmaceutically acceptable additive according to a conventional method and, preferably, formulated into an imaging agent for diagnosis in a solution form by dissolving it in a physiologically acceptable aqueous solvent.

When the polynuclear type metal complex compound of the present invention is used for imaging agent for diagnosis, the dose to be used is selected depending upon a particular use of image diagnosis. For example, for MRI diagnosis, the dose is generally 0.0001 to 10 mmol/kg, preferably, 0,005 to 0.5 mmol/kg in terms of the metal ion. For X-ray diagnosis, the dose is 0.01 to 20 mmol/kg, preferably, 0.1 to 10 mmol/kg in terms of the metal ion. Further, for radiation diagnosis, the dose is 370–18500 MBq in terms of radioactivity. Usually, the imaging agent is administered intravenously and, in some cases, can be administered orally or intra-arterially.

The retention in blood of the polynuclear type metal complex compound of the present invention is in a clinically effective range (half-life period in blood of 0.5 to 5 hours). Thus, it is possible to suitably combine the imaging agent with a particular MRI apparatus having a different magnetic field intensity by appropriately selecting the polymerization degree of the amino oligosaccharide. For example, in the case of low magnetic field intensity MRI apparatus, the use of the imaging agent for diagnosis having a relatively long retention time in blood is preferred in order to improve the collection efficacy of proton relaxation effect by the imaging agent. In addition, the polynuclear type metal complex compound of the present invention has the advantage of having the higher contrast efficacy per unit dose. For example, when Gd is contained as the metal ion, the shortening effect of the relaxation time per molecule is superior to that of DTPA-Gd, the polynuclear type metal complex compound can be used advantageously as a MRI diagnostic agent. This improves the detection efficacy in an another sense in the diagnosis by low magnetic field MRI apparatus having a low collection efficacy of proton relaxation effect, resulting in the shortening of the imaging time. Further, when the same contrast effect as that of DTPA-Gd in an apparatus having the same magnetic field intensity is required, the polynuclear type metal complex compound of the present invention can be administered in a smaller dose than DTPA-Gd and, therefore, becomes more advantageous in view of safety. To the contrary, at the same dose, the polynuclear metal complex compound of the present invention provides more informations about the living body than DTPA-Gd, resulting in the improvement in the clinical usefulness. Therefore, the present invention can provide the imaging agent having suitable retention in blood, matching with the magnetic field intensity of a MRI apparatus and imaging conditions, as well as effective contrast effect.

Further, since the polynuclear type metal complex compound of the present invention shows the suitable retention in blood, the evaluation of the blood vessel distribution image (vascularity) becomes possible. Therefore, the imaging agent for diagnosis of the present invention can image the blood vessel without pulse sequence which is particularly necessary for recently remarkably advanced MR angiography, and the agent is also useful as a diagnostic imaging agent for intravenous injection.

Since the polynuclear type metal complex compound of the present invention has good solubility in water, the compound itself can be prepared as a solution containing the compound in a high concentration. Accordingly, a solubilizer is not necessarily required upon preparation of the solution. In addition, the metal complex compound of the present invention is a polynuclear compound and, therefore, can decrease the total molality in the preparation of a solution in comparison with the mononuclear compound, which results in the decrease in osmotic pressure. These alleviate the load to volume of the circulatory system or body fluid equilibrium upon administration in the living body, which resulting in advantage in the safety.

As described herein above, the imaging agent of the present invention comprises the polynuclear type metal complex wherein a plurarity of metal ions are chemically bonded thereto via a plurality of the bifunctional ligands which are chemically bonded to the chitosan-oligosaccharide or galactosamino-oligosaccharide. By using this novel and special polynuclear type metal complex compound, image diagnosis such as MRI diagnosis, X-ray diagnosis, radiation diagnosis and the like can be efficiently carried out.

The following Examples and Tests further illustrate the present invention in detail but are not to be construed to limit the scope thereof.

The abbreviations used in Examples and Tests mean as follows:
GPEN: galactosamino-pentamer
CHEX: chitosan-hexamer
GTRI: galactosamino-trimer
CPEN: chitosan-pentamer
DTPA: diethylenetriaminepentaacetic acid
DTES: 1-(p-isothiocyanatebenzyl)-diethylenetriaminepentaacetic acid
DOTA: 1,4,7,10-tetraazacyclododecane-1,4,7,10-tetraacetic acid
ICB-DOTA: 2-(p-isothiocyanatebenzyl)-1,4,7,10-tetraazacyclododecane-1,4,7,10-tetraacetic acid.

EXAMPLE 1

Synthesis of GPEN-DTES

GPEN (0.39 g; 0.43 mmol) was dissolved in 0.1M phosphate buffer (pH 7.0) (2 ml) and DTES (0.70 g; 1.3 mmol) was added thereto. 10N Aqueous solution of sodium hydroxide was added thereto to adjust pH to about 12, and the mixture was reacted at room temperature for 24 hours with stirring. To the reaction mixture was added 7N hydrochloric acid to neutralize to obtain crude GPEN-DTES.

A portion of the reaction mixture (50 μl) was taken out and 0.1M citrate buffer (pH 5.9) (100 μl) and a solution (50 μl) of indium chloride (In-111) were admixed with the reaction mixture. The ratio of GPEN-DTES-In-111 and DTES-In-111 was determined by thin layer chromatography and it was confirmed that 1.4 molecules of DTES were bonded per GPEN molecule.

The above reaction mixture was concentrated and purified by preparative thin layer chromatography (silica gel) to obtain GPEN-DTES (0.24 g).

Proton-nuclear magnetic resonance (NMR) spectrum (solvent/$D_2O$, 270MHz): 2.10–3.37 ppm (10H, m, $CH_2$), 3.49–4.55 ppm, 4.88–5.59 ppm (m, CH, CH$_2$ and NH), 4.22 ppm(1H, bs, N-CH), 7.07–7.40 ppm (4H, m, benzene ring)

Infrared absorption (IR) spectrum (KBr tablet): 810 cm$^{-1}$ (CH of benzene ring), 1100 cm$^{-1}$ (OH), 1400cm$^{-1}$ (CH$_2$), 1590 cm$^{-1}$ (COOH)

EXAMPLE 2

Synthesis of GTRI-DTES

GTRI (6.4 mg; 0.01 mmol) was dissolved in 0.1M phosphate buffer (pH 7.0) (1 ml) and DTES (17.4 mg; 0.03 mmol) was added thereto. 10 N Aqueous solution of sodium hydroxide was added thereto to adjust pH to about 12, and the mixture was reacted at room temperature for 24 hours with stirring. To this reaction mixture was added 7N hydrochloric acid to neutralize to obtain crude GTRI-DTES.

A portion of the reaction mixture (50 µl) was taken out and 0.1M citrate buffer (pH 5.9) (100 µl) and a solution (50 µl) of indium chloride (In-111) were admixed with the reaction mixture. The ratio of GTRI-DTES-In-111 and DTES-In-111 was determined by thin layer chromatography and it was confirmed that 3 molecules of DTES were bonded per GTRI molecule.

The above reaction mixture was concentrated and purified by preparative thin layer chromatography (silica gel) to obtain GTRI-DTES (11.0 mg).

Proton-NMR spectrum (solvent/D$_2$O, 270 MHz): 2.20–3.58 ppm (10H, m, CH$_2$), 3.58–4.63 ppm, 4.95–5.65 ppm (m, CH, CH$_2$ and NH), 4.30 ppm (1H, bs, N-CH), 7.15–7.45 ppm (4H, m, benzene ring)

IR spectrum (KBr tablet): 810 cm$^{-1}$ (CH of benzene ring), 1070 cm$^{-1}$ (OH), 1400 cm$^{-1}$ (CH$_2$), 1625 cm$^{-1}$ (COOH)

EXAMPLE 3

Synthesis of CPEN-DTPA

CPEN (0.08 g; 0.08 mmol) was dissolved in water (2 ml) and 4N aqueous solution (1.2 ml) of sodium hydroxide was added thereto. DTPA anhydride (0.57 g; 1.59 mmol) was added thereto immediately, and the mixture was reacted at room temperature for 3 hours with stirring to obtain crude CPEN-DTPA.

A portion of the reaction mixture (0.2 ml) was taken out and 0.1M citrate buffer (pH 5.9) (0.2 ml) and a solution (0.025 ml) of indium chloride (In-111) were admixed with the reaction mixture. The ratio of CPEN-DTPA-In-111 and DTPA-In-111 was determined by thin layer chromatography and it was confirmed that 4.5 molecules of DTPA were bonded per CPEN molecule.

The above reaction mixture was concentrated and purified by preparative thin layer chromatography (silica gel) to obtain CPEN-DTPA (0.08 g).

Proton-NMR spectrum (solvent/D$_2$O, 270 MHz): 2.0 ppm (H, s, CH$_2$), 3.1–3.3 ppm (m, CH$_2$), 3.4–3.6 ppm (m, CH$_2$), 3.8 ppm(4H, s, CH$_2$)

IR spectrum (KBr tablet): 1090 cm$^{-1}$ (OH), 1400 cm$^{-1}$ (CH$_2$), 1600 cm$^{-1}$ (COOH)

EXAMPLE 4

Synthesis of CPEN-(ICB-DOTA)

CPEN and ICB-DOTA are dissolved in 0.1M phosphate buffer (pH 7.0), and the solution is reacted at room temperature while maintaining pH at 12 to obtain CPEN-(ICB-DOTA).

EXAMPLE 5

Preparation of GPEN-DTES-Gd solution

GPEN-DTES (0.30 g; 0.18 mmol) was dissolved in distilled water (2 ml). Gadolinium chloride hexahydride (0.06 g; 0.17 mmol) was added thereto and the mixture was reacted at room temperature with stirring to obtain GPEN-DTES-Gd. The absence of free Gd was confirmed by a color developing reaction using Xylenol Orange as a pigment indicator.

Gd concentration (ICP emission analysis): 75.1 mM

EXAMPLE 6

Synthesis of Gd complex

Gd complex of the relevant compound is obtained by the same manner as that described in Example 5 except that GPEN-DTES is substituted by GTRI-DTES, CPEN-DTPA and CPEN-(ICB-DOTA).

EXAMPLE 7

Preparation of GPEN-DTES-In-111 solution

GPEN-DTES (10 mg) was dissolved in distilled water (0.5 ml) and 0.1M citrate buffer (pH 5.9) (1 ml) was added thereto. A solution (0.5 ml; 148 MBeq) of indium chloride (In-111) was admixed to obtain GPEN-DTES-In-111. Its radiochemical purity was 100%.

EXAMPLE 8

Synthesis of CHEX-DTPA-Bi

CHEX-DTPA (0.45 g; 0.13 mmol) synthetized according to the same manner as that described in Example 3 was dissolved in distilled water (30 ml). Bismuth chloride (0.28 g; 0.88 mmol) was added thereto, pH was adjusted to about neutral by addition of 4N aqueous solution of sodium hydroxide. The mixture was reacted at 60° C. for 18 hours with stirring. The insoluble materials were filtered off and the filtrate was purified through a desalting apparatus (manufactured by Asahikasei K. K., Japan). The purified solution was concentrated and dried to obtain CHEX-DTPA-Bi (0.54 g). The absence of free Bi was confirmed by a color developing reaction using Xylenol Orange as a pigment indicator.

IR spectrum (KBr tablet): 1070 cm$^{-1}$ (OH), 1393 cm$^{-1}$ (CH$_2$), 1458 cm$^{-1}$ (CONH), 1582 cm$^{-1}$ (COO$-$)

Quantitative analysis of Bi (ICP emission analysis): 0.11 g

Test 1

Relaxivity of GPEN-DTES-Gd and GTRI-DTES-Gd (in vitro test)

An appropriate amount of GPEN-DTES-Gd and GTRI-DTES-Gd were dissolved in distilled water. The relation to water proton exposed to these compounds was determined as a proton relaxation time (T$_1$ and T$_2$, msec) at room temperature (24° to 26° C.) using NMR (6.35T, manufactured by Nihondenshi K. K., Japan). Respective relaxation times are shown in Tables 1 and 2.

TABLE 1

| Relaxation time of GPEN-DTES-Gd | | |
|---|---|---|
| Concentration (mM) | T$_1$ (msec) | T$_2$ (msec) |
| 2.3 | 55 | 26 |
| 0 | 3275 | 2208 |

TABLE 2

| Relaxation time of GTRI-DTES-Gd | | |
|---|---|---|
| Concentration (mM) | $T_1$ (msec) | $T_2$ (msec) |
| 2.9 | 46 | 26 |
| 0 | 3275 | 2208 |

GPEN-DTES-Gd (2.3 mM) shortened remarkably the $T_1$ value of water about 60 times and the $T_2$ value of water 85 times. And GTRI-DTES-Gd (2.9 mM) shortened remarkably the $T_1$ value of water about 70 times and the $T_2$ value about 85 times. The relaxivity on $T_1$ and $T_2$ [each $R_1$ and $R_2$, $(mM \cdot S)^{-1}$] were calculated based on the values in Tables 1 and 2. The results are shown in Table 3.

TABLE 3

| Relaxivity of GPEN-DTES-Gd and GTRI-DTES-Gd | | |
|---|---|---|
| Compound | $R_1$ (mM · S)$^{-1}$ | $R_2$ (mM · S)$^{-1}$ |
| GPEN-DTES-Gd | 7.6 | 16.2 |
| GTRI-DTES-Gd | 7.4 | 13.1 |
| DTPA-Gd | 3.9 | 4.8 |

GPEN-DTES-Gd and GTRI-DTES-Gd have good in vitro relaxation effect and the effect is predominantly higher than that of DTPA-Gd (also shown in Table 3) which is mononuclear complex, determine according to the same manner. The results clearly show the effectiveness of GPEN-DTES-Gd and GTRI-DTES-Gd.

Test 2

Relaxation time of GPEN-DTES-Gd in blood in mouse after intravenous administration (ex vivo test)

GPEN-DTES-Gd (Gd concentration: 75 mM) (0.025 mmol/kg in terms of Gd) was administered to a thiopental anesthetized ICR female mouse (body weight: 44 g) through the tail vein. At 15 minutes after administration, the blood was taken from the aorta descendence, and the relaxation time ($T_1$, msec) of the blood at room temperature (24° to 26° C.) was determined with a 6.35T NMR apparatus (manufactured by Nihondenshi K. K., Japan).

As a control, blood was taken from the aorta descendence of a thiopental anesthetized ICR female mouse (body weight: 55 g) and, according to the same manner, the relaxation time was determined. The results are Table 4.

TABLE 4

| Relaxation time of GPEN-DTES-Gd in blood | |
|---|---|
| Administered compound | $T_1$ in blood (msec) |
| GPEN-DTES-Gd | 769 |
| control | 1769 |

$T_1$ relaxation time of GPEN-DTES-Gd in blood is about 2.3 times effect compared with that of the control mouse and it has been found that the relaxation time of the blood is effectively shortened.

Test 3

Contrast enhancement of the heart in rat at 1 hour after intravenously administration of GPEN-DTES-Gd (in vivo test)

A solution of GPEN-DTES-Gd (Gd concentration: 75.1 mM) (0.094 mmol/kg in terms of Gd) was administered to a thiopental anesthetized Sprague-Dawley female rat (214 g, 9-weeks old) through a cannula fixed to femoral vein. At 1 hour after administration, the animal was sacrificed by administration of pentobarbital solution (1 ml) through the above cannula, fixed at prone position in the magnetic field of a MRI spectrometer. MRI measurement (transverse sectional view) of the chest region including the heart was carried out.

As a control, DTPA-Gd (MAGNEVIST®) was administered to a Sprague-Dawley female rat (body weight: 204 g, 9-weeks old) through a cannula fixed at femoral vein (0.1 mmol/kg) and the measurement (transverse sectional view) of the chest region including the heart was carried out as described above.

The apparatus was SIGMA (manufactured by GE, U.S.A.) with magnetic field intensity of 1.5T and, as an imaging coil, a 26 cm φ bird-cage type head QD coil was used. Imaging was carried out according to spin echo method of $T_1$ weighted (TR/TE, 600/30 msec) under the condition of 10 mm in slice thickness, a resolution of 256×128.

The signal intensity from the rat to which GPEN-DTES-Gd was administered was found to be about 1.8 times higher than that of the rat to which MAGNEVIST® was administered when comparing the signal intensity from the same part of the heart, The superiority in retention in blood of GPEN-DTES-Gd over that of DTPA-Gd together with the dose of Gd demonstrated the advantages of the present invention.

Test 4

Radioactivity-distribution in blood and urine after intravenous administration of GPEN-DTES-In-111 (in vivo test)

Sprague-Dawley female rats (three rats/mesurement time) (body weight: 110 to 130 g) were anesthetized with thiopental and GPEN-DTES-In-111 solution prepared in Example was administered through the tail vein (50 μl/rat). The animals were sacrificed by dehematization at 0.25, 0.5, 1, 3, 6 and 24 hours after administration. The blood and bladder were removed and the radioactivity was measured. The radioactivity distribution ratio in blood and urine at each measurement time are shown in Table 5.

TABLE 5

| Radioactivity distribution ratio of GPEN-DTES-In-111 in blood and urine | | |
|---|---|---|
| Time (hr) | Blood (%/dose) | Urine (%/dose) |
| 0.25 | 4.63 ± 1.65 | 51.23 ± 1.40 |
| 0.5 | 2.63 ± 0.86 | 66.07 ± 3.45 |
| 1.0 | 2.72 ± 0.40 | 77.13 ± 3.36 |
| 3.0 | 1.92 ± 1.06 | 81.43 ± 6.23 |
| 6.0 | 0.67 ± 0.35 | 87.04 ± 4.68 |
| 24.0 | 0.16 ± 0.12 | 90.12 ± 3.57 |

As seen from the results in Table 5, the half-life period of GPEN-DTES-In-111 in blood was about 55 minutes and was found to be clinically effective retention in blood. Since excretion into the urine was good, there was no problem of residence in the body.

What is claimed is:

1. An imaging agent for X-ray diagnosis comprising a compound composed of a polynuclear type Compound of the formula I or II:

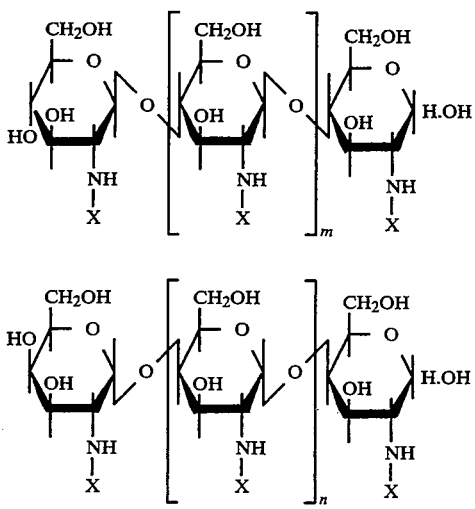

wherein each X is a hydrogen atom or a bifunctional ligand, at least one of them is a bifunctional ligand and each of m and n is an integer of 1 to 6, and at least one metal ion being coordinated with at least one bifunctional ligand moiety, said metal ion being a radiopaque metal ion.

2. The imaging agent for X-ray diagnosis according to claim 1, wherein the bifunctional ligand is derived from diethylenetriaminepentaacetic acid or 1,4,7,10-tetraazacyclododecane-1,4,7,10-tetraacetic acid.

3. The imaging agent for x-ray diagnosis according to claim 1, wherein said metal ion is a Bi, Pb, or Os ion.

4. The imaging agent for X-ray diagnosis according to claim 1, the retention time in blood of which is 0.5 to 5 hours as half-life period.

5. The imaging agent for x-ray diagnosis according to claim 1, wherein said metal ion is selected from the group consisting of lanthanide element ions having the atomic numbers ranging from 57–70 and the ions of the elements having the atomic numbers 56, 76, 82, and 83.

6. An x-ray diagnosis method which comprises administering to a subject a diagnostically effective amount of the compound as claimed in claim 1 and performing an x-ray diagnostic procedure on said subject.

7. An x-ray diagnosis method which comprises administering to a subject a diagnostically effective amount of the compound as claimed in claim 1 wherein the bifunctional ligand is derived from diethylenetriaminepentaacetic acid or 1,4,7,10-tetraazacyclododecane-1,4,7,10-tetraacetic acid and performing an x-ray diagnostic procedure on said subject.

8. An x-ray diagnosis method which comprises administering to a subject a diagnostically effective amount of the compound as claimed in claim 1, wherein said metal ion is a Bi, Pb, or Os Ion and performing an x-ray diagnostic procedure on said subject.

9. An x-ray diagnosis method which comprises administering to a subject a diagnostically effective amount of the compound as claimed in claim 1, wherein said metal ion is selected from the group consisting of lanthanide element Ions having the atomic numbers ranging from 57–70 and the ions of the elements having the atomic numbers 56, 76, 82, and 83, and performing an x-ray diagnostic procedure on said subject.

* * * * *